(12) United States Patent
Zhang et al.

(10) Patent No.: US 12,096,942 B2
(45) Date of Patent: Sep. 24, 2024

(54) HEMOSTASIS AND SUTURING CONJOINED DUAL-CLAMP CAPABLE OF PASSING THROUGH CHANNEL OF DIGESTIVE ENDOSCOPE AND OPERATION METHOD

(71) Applicants: MICRO-TECH (NANJING) CO., LTD., Jiangsu (CN); Qiang Zhang, Guangzhou (CN)

(72) Inventors: Qiang Zhang, Guangzhou (CN); Yang Bai, Guangzhou (CN)

(73) Assignees: MICRO-TECH (NANJING) CO., LTD., Nanjing (CN); Qiang Zhang, Guangzhou (CN)

( * ) Notice: Subject to any disclaimer, the term of this patent is extended or adjusted under 35 U.S.C. 154(b) by 691 days.

(21) Appl. No.: 17/317,109

(22) Filed: May 11, 2021

(65) Prior Publication Data

US 2021/0259700 A1    Aug. 26, 2021

Related U.S. Application Data

(63) Continuation of application No. PCT/CN2019/121006, filed on Nov. 26, 2019.

(30) Foreign Application Priority Data

Nov. 29, 2018 (CN) .......................... 201811440727.6

(51) Int. Cl.
*A61B 17/122* (2006.01)
*A61B 17/04* (2006.01)

(52) U.S. Cl.
CPC ...... *A61B 17/1222* (2013.01); *A61B 17/0469* (2013.01)

(58) Field of Classification Search
CPC ............ A61B 17/1222; A61B 17/0469; A61B 17/0487; A61B 2017/0488;

(Continued)

(56) References Cited

U.S. PATENT DOCUMENTS 10,905,411 B2 * 2/2021 Racenet ............. A61B 17/0469
2014/0142597 A1  5/2014 Winkler et al.
(Continued)

FOREIGN PATENT DOCUMENTS

CN    105615938 A    6/2016
CN    106419992 A    2/2017
(Continued)

OTHER PUBLICATIONS

International Search Report issued on Jan. 23, 2020 in corresponding International Application No. PCT/CN2019/121006; 6 pages.

(Continued)

*Primary Examiner* — Sarah A Long
*Assistant Examiner* — James R McGinnity
(74) *Attorney, Agent, or Firm* — Maier & Maier, PLLC

(57) ABSTRACT

A hemostasis and suturing conjoined dual-clamp capable of passing through a channel of a digestive endoscope and an operation method, the dual-clamp including a handle, a clamping assembly and a driving assembly. The clamping assembly includes a clamping holder and two clamping portions, and the driving assembly is detachably connected to the clamping assembly. A hemostasis and suturing conjoined dual-clamp capable of passing through a channel of a digestive endoscope and an operation method, two clamping arms of the dual-clamp are able to individually open, clamp and close, have a function of double-sided clamping and closing a large defective wound, and are able to be conveniently separated from the driving assembly, overcoming the defects that conventional hemostatic clamps can only perform one-sided clamping, thereby it is difficult to treat defective wounds that are large or in difficult operating sites.

19 Claims, 6 Drawing Sheets

(58) Field of Classification Search
CPC ... A61B 2017/049; A61B 17/10; A61B 17/12;
A61B 2017/12004; A61B 17/122; A61B
2017/1225; A61B 17/1227; A61B 17/128;
A61B 17/1285; A61B 17/08
See application file for complete search history.

(56) References Cited

U.S. PATENT DOCUMENTS

| | | |
|---|---|---|
| 2015/0190136 A1 | 7/2015 | Cohen et al. |
| 2015/0282813 A1 | 10/2015 | Litscher et al. |

FOREIGN PATENT DOCUMENTS

| | | | |
|---|---|---|---|
| CN | 206273250 U | | 6/2017 |
| CN | 107115130 A | | 9/2017 |
| CN | 206534673 U | | 10/2017 |
| CN | 107550535 A | | 1/2018 |
| CN | 107684448 A | | 2/2018 |
| CN | 109350171 A | | 2/2019 |
| CN | 209629747 U | | 11/2019 |
| CN | 206239447 U | * | 2/2021 |
| WO | 2011/022246 A1 | | 2/2011 |

OTHER PUBLICATIONS

Office Action issued on Nov. 25, 2023, in corresponding Chinese Application No. 201811440727.6, 11 pages, including partial English translation.

* cited by examiner

HEMOSTASIS AND SUTURING CONJOINED DUAL-CLAMP CAPABLE OF PASSING THROUGH CHANNEL OF DIGESTIVE ENDOSCOPE AND OPERATION METHOD

CROSS-REFERENCE TO RELATED APPLICATIONS

This application is a continuation of International Application No. PCT/CN2019/121006, filed on Nov. 26, 2019, which claims priority to Chinese Patent Application No. 201811440727.6, filed with the China National Intellectual Property Administration (CNIPA) on Nov. 29, 2018, entitled "Hemostasis and suturing conjoined dual-clamp capable of passing through channel of digestive endoscope and operation method". Both of the above applications are hereby incorporated by reference in their entireties.

TECHNICAL FIELD

The present disclosure relates to the field of medical equipment for closure of tissue defects under an endoscope, more particularly to, a hemostasis and suturing conjoined dual-clamp capable of passing through a channel of a digestive endoscope and an operation method.

BACKGROUND

With the development of endoscope minimally invasive technology, some digestive tract diseases that previously require surgical laparotomy or laparoscopic treatment, such as early digestive tract tumors, all can be treated with digestive endoscopy minimally invasive. In a process of endoscope minimally invasive surgery, digestive tract mucosal defectives (including digestive tract bleeding and perforation) are the most common problems. At present, the main defective suture methods used are endoscope clip, nylon cord combined with endoscope clip purse-string suture and Over-the-Scope Clip (OTSC). The endoscope clip is simple to use and relatively inexpensive, but it is difficult to repair defectives that are large or in difficult sites. OTSC was invented by foreign experts, it is expensive and complicated to operate, which requires preliminary training before it is used.

SUMMARY

An object of embodiments of the present disclosure is that, for example, the present disclosure provides a hemostasis and suturing conjoined dual-clamp capable of passing through a channel of a digestive endoscope and an operation method. Two clamping arms of the dual-clamp are able to individually open, clamp and close, have a function of double-sided clamping and closing a large defective wound, and are able to be conveniently separated from a driving assembly, overcoming the defectives that conventional hemostatic clamps can only perform one-sided clamping, thereby it is difficult to treat defective wounds that are large or in difficult operating sites.

The embodiments of the present disclosure are implemented as follows:

the present disclosure provides a hemostasis and suturing conjoined dual-clamp capable of passing through a channel of a digestive endoscope, including: a handle, a clamping assembly and a driving assembly, where the clamping assembly is provided at a front end of the handle, the clamping assembly includes a clamping holder and two clamping portions, the two clamping portions are provided around two sides of the clamping holder and are rotatably connected to the clamping holder, the driving assembly is configured to drive the two clamping portions to open and close relative to the clamping holder, respectively;

the driving assembly is detachably connected to the clamping assembly.

Optionally, the clamping holder includes a central claw rod, a first connecting portion and a second connecting portion that are integrally formed and sequentially connected, the second connecting portion is provided with a tail cavity with openings at two ends; and the two clamping portions both pass through the tail cavity and are located at two sides of the first connecting portion, and the two clamping portions are rotatably fitted with the first connecting portion.

Optionally, the central claw rod is provided with a first fixing hole, and each clamping portion is provided with a second fixing hole: the clamping holder further includes a fixing pin, where the fixing pin simultaneously passes through the first fixing hole and two second fixing holes to connect with the central claw rod and the clamping portion.

Optionally, a peripheral surface of the central claw rod is provided with two avoidance grooves, and the clamping portion is protrudingly provided with a catching portion, and when the clamping portion is closed, two catching portions on the two clamping portions are respectively caught into the two avoidance grooves.

Optionally, the clamping portion includes a clamping arm and a connecting arm, where the connecting arm is movably connected to the clamping arm, the driving assembly includes a driving member, where the driving member is movably connected to the connecting arm, and the driving member is configured to drive the connecting arm to move to drive the clamping arm to rotate relative to the clamping holder.

Optionally, the driving assembly is configured to drive the connecting arm to reciprocate linearly, so that the connecting arm drives the clamping arm to rotate relative to the clamping holder.

Optionally, the clamping arm includes a clamping claw and a third connecting portion which are connected, where the third connecting portion is provided with a third sliding chute, an extending direction of the third sliding chute has an angle with a sliding direction of the connecting arm, and the connecting arm is slidably fitted with the third sliding chute, and when the driving assembly drives the connecting arm to move linearly, the connecting arm slides in the third sliding chute and meanwhile drives the clamping arm to rotate.

Optionally, the connecting arm is provided with a front end connecting hole, and the clamping assembly further includes a first pin shaft, where the first pin shaft simultaneously passes through the tail end connecting hole and the third sliding chute, to connect with the third connecting portion and the connecting arm.

Optionally, the clamping assembly further includes a locking piece, where the locking piece is connected to the clamping holder and forms two independent sliding channels together with the clamping holder, and the two connecting arms respectively pass through the two sliding channels, and the connecting arm and clamping holder are relatively fixed on a circumferential direction of the clamping holder.

Optionally, the locking piece is snap-fitted with the clamping holder.

Optionally, the clamping assembly further includes an anti-return structure, the anti-return structure is provided between the connecting arm and the locking piece and is configured to restrict the connecting arm from driving the clamping arm to rotate from a closed state to an open state.

Optionally, the anti-return structure includes an elastic piece and a locking platform, where the locking piece has two opposite board surfaces, and each board surface is provided with the locking platform: each connecting arm is connected to one side of the elastic piece, and when the clamping arm is closed, the other side of the elastic piece is located between the locking platform and the driving assembly, and the other side of the elastic piece is inclined in a direction away from the connecting arm, so that an orthographic projection of the elastic piece in a sliding direction of the connecting arm at least partially overlaps with the locking platform, to restrict the connecting arm from passing over the elastic piece in a direction close to the elastic piece.

Optionally, the driving assembly includes two driving members, where the two driving members are fitted with the two connecting arms one by one, each driving member is provided with a sliding chute, the clamping assembly further includes a second pin shaft, the driving assembly and the connecting arm are both connected to the second pin shaft, and the second pin shaft passes through the sliding chute and is slidably fitted with the sliding chute; and the driving assembly is configured to press the elastic piece to unlock the elastic piece from the locking platform when sliding relative to the connecting arm, and drive the connecting arm to move linearly through the second pin shaft after unlocking the elastic piece from the locking platform are unlocked, to enable the clamping arm to rotate.

Optionally, the elastic piece and the connecting arm are integrally formed.

Optionally, the driving member is provided with a fracture region, and the fracture region is located at one side of the sliding chute close to the connecting arm.

Optionally, the conjoined dual-clamp further includes a clamping base, and the clamping base is detachably connected to the clamping holder.

Optionally, the conjoined dual-clamp further includes a hook, and the driving assembly is detachably connected to the clamping assembly through the hook.

Optionally, the driving assembly further includes two flexible shafts, two hook arms of the hook are respectively provided with releasing rings, one ends the two flexible shafts respectively pass through corresponding releasing rings, and the other ends of the two flexible shafts are respectively connected to the two clamping portions of driving member.

The present disclosure also provides an operation method of the hemostasis and suturing conjoined dual-clamp capable of passing through the channel of the digestive endoscope, where the operation method includes an opening method, a closing method, a locking method, and a disassembling method of the dual-clamp;

the opening method is: the driving member is pushed to move forward, and the driving member moves forward to drive the connecting arm to move forward, so that the connecting arm rotates and opens to facilitate subsequent clamping of a human mucosal tissue;

the closing method is: the driving member is pushed to move backward to drive the connecting arm to move backward, so that the connecting arm rotates and is closed, and the clamping arm is closed and clamps the human mucosal tissue;

the locking method is: after the closing step is completed, the driving member is continuously pulled backward, the elastic piece of the connecting arm rebounds and is locked on the locking platform of the locking piece after losing the pressure of the driving member, and the driving member and the clamping arm are kept in a relative position and locked; and the disassembling method is: after the locking step, the driving member is continuously to be pulled to move backward with a greater pulling force to make the driving member fractured, and a connection between the driving assembly and the clamping assembly is dismantled and the driving assembly and the clamping assembly are separated.

Furthermore, the opening method is: the driving member is pushed to move forward, so as to sequentially the flexible shaft and the driving assembly to move forward, the driving member moves forward to pass through a channel of the locking piece, and presses down the elastic piece on the connecting arm to release the locking with the locking platform of the locking piece, the connecting arm moves forward to push the clamping arm to rotate so as to open an opening formed with the central claw rod of the clamping holder, to facilitate the subsequent clamping of the human mucosal tissue;

the closing method is: a slip ring is pulled backward so as to sequentially pull the flexible shafts, the driving member and the connecting arm to move backward, to drive the clamping arm to rotate and close an opening formed with the central claw rod of the clamping holder, to clamp the human mucosal tissue by closing;

the locking method is: after the closing step is completed, the driving member is continuously pulled backward, the driving member moves backward relative to the connecting arm, the elastic piece of the connecting arm rebounds and is locked on the locking platform of the locking piece after losing the pressure of the driving member, and the driving member and the clamping arm are kept in a relative position and locked; and the disassembling method is: after the locking step is completed, the driving member is continuously pulled backward with a greater pulling force, and the fracture region of the driving member is fractured, a tail end of the driving member that continues to move backward sequentially drives the releasing rings and the hook to move backward until the hook is separated from a through hole of the clamping holder and the clamping base, and then a connection between the clamping holder and the clamping base is dismantled and the clamping holder and the clamping base are separated.

Compared with the prior art, the beneficial effects of the present disclosure include, for example:

the present disclosure includes two clamping portions and a clamping holder, where the two clamping portions are provided around two sides of the clamping holder and being rotatably connected to a front end of the clamping holder, and the driving assembly drives the two clamping portions to open and close relative to the clamping holder respectively. The dual-clamp of the present disclosure can directly pass through a working channel of the endoscope and achieve a dual-sided clamping. With regard to defective wounds, the clamping portion of one side of the dual-clamp and the clamping holder can be first used to clamp an edge of one side of the wound, and then be pulled to an edge of another side of the wound, and then the clamping portion of the other side of the dual-clamp and clamping holder clamp an edge of the other side of the wound, and finally realize a clamping and closing of the defective wound, which is simple and quick, and effectively solves the problem that conventional hemostatic clamps can only perform one-sided clamping, so that it is difficult to treat defective wounds that are large or in difficult operating sites, and can be conveniently separated from the driving assembly, which greatly facilitates the surgeon's operation of doctors.

BRIEF DESCRIPTION OF THE DRAWINGS

In order to more clearly illustrate the technical solutions in embodiments of the present disclosure, the drawings needed to be used in the embodiments will be briefly described below. It should be understood that the following drawings only show some embodiments of the present disclosure, so they should not be regarded as a limitation of the scope. For those skilled in the art, they can also obtain other related drawings according to these drawings without any creative efforts.

DETAILED DESCRIPTION OF THE EMBODIMENTS

Figure 1:
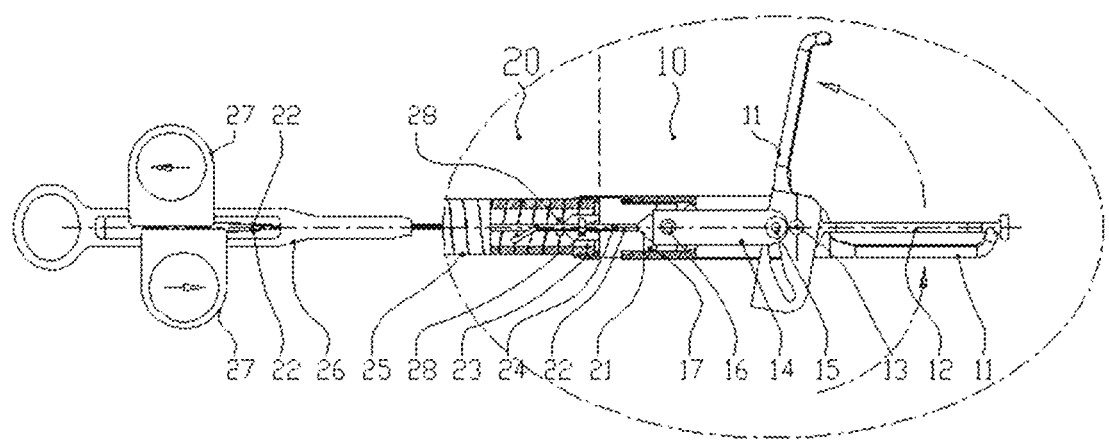
FIG. 1 is a first structural schematic diagram of the present disclosure (front view)

In order to make the objectives, technical solutions and advantages of the embodiments of the present disclosure more clear, the technical solutions in the embodiments of the present disclosure will be clearly and completely described in combination with the drawings in the embodiments of the present disclosure. Obviously, the described embodiments are part of the embodiments of the present disclosure, but not all of the embodiments. The components of the embodiments of the present disclosure generally described and illustrated in the drawings herein may be arranged and designed in a variety of different configurations.

Therefore, the following detailed description of the embodiments of the present disclosure provided in the drawings is not intended to limit the claimed scope of the present disclosure, but merely represents selected embodiments of the present disclosure. Based on the embodiments in the present disclosure, all other embodiments obtained by those skilled in the art without any creative efforts shall fall within the protection scope of the present disclosure.

It should be noted that similar reference numerals and letters in the following drawings indicate similar items. Therefore, once a certain item is defined in one drawing, it does not need to be further defined and explained in the subsequent drawings.

In the description of the present disclosure, it should be noted that if orientations or positional relationships indicated by terms "center", "up", "down", "left", "right", "vertical", "horizontal", "in", "out" and the like appear, they are based on orientations or positional relationships shown in the drawings, or orientations or positional relationships usually placed when products of the disclosure are used. It is only for the convenience of describing the present disclosure and simplifying the description, rather than indicating or implying that the device or element referred to must have a specific orientation, be constructed and operated in a specific orientation, and therefore cannot be understood as limitations of the present disclosure.

In addition, if terms "first", "second", "third", and the like appear, they are only used for distinguishing description, and cannot be understood as indicating or implying relative importance.

In addition, if terms "horizontal", "vertical", "overhanging", and the like appear, they does not mean that the component is required to be absolutely horizontal or overhanging, but can be slightly inclined. For example, "horizontal" only means that the direction thereof is more horizontal than "vertical", it does not mean that this structure must be completely horizontal, but can be slightly inclined.

In the description of the present disclosure, it should also be noted that, unless otherwise clearly defined and limited, terms "provide", "install", "connect", "connection", and the like should be interpreted in a broad sense, for example, it may be a fixed connection, and may also be a detachable connection, or an integral connection; may be a mechanical connection, and may also be an electrical connection; may be a direct connection, and may also be an indirect connection through an intermediate medium, and may be a connection inside two elements. For those skilled in the art, the specific meanings of the above-mentioned terms in the present disclosure can be understood according to specific situations.

It should be noted that, in the case of no conflict, the features in the embodiments of the present disclosure can be combined with each other.

The present disclosure provides a hemostasis and suturing conjoined dual-clamp capable of passing through a channel of a digestive endoscope and an operation method, as shown in FIGS. 1-15, including a handle 26, a clamping assembly 10 and a driving assembly 20, the clamping assembly is provided at a front end of the handle, the clamping assembly includes a clamping holder 12 and two clamping portions, the two clamping portions are provided around two sides of the clamping holder 12 and are rotatably connected to the front end of the clamping holder 12, and the driving assembly 20 is configured to drive the two clamping portions to rotate to open and close relative to the clamping holder 12.

The driving assembly 20 is detachably connected to the clamping assembly 10.

Figure 9:
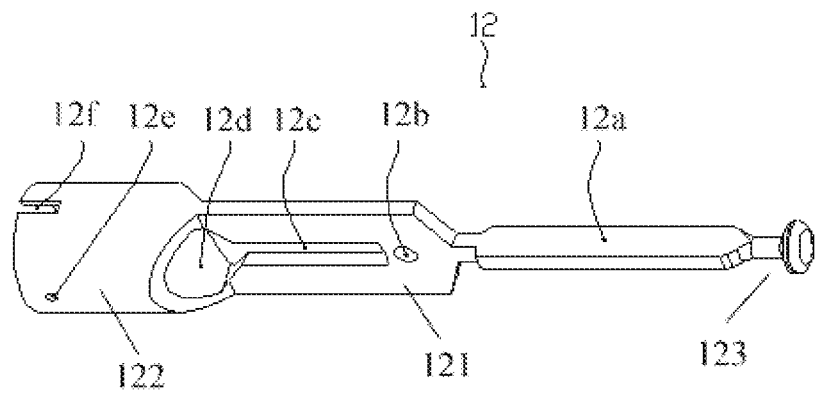
FIG. 9 is a structural schematic diagram of a clamping holder of the present disclosure.
Figure 10:
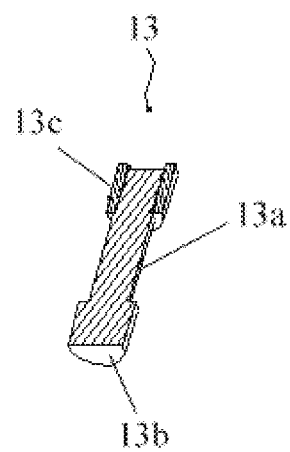
FIG. 10 is a structural schematic diagram of a fixing pin of the present disclosure.

Referring to FIG. 9, optionally, the clamping holder 12 includes a central claw rod 12a, a first connecting portion 121 and a second connecting portion 122 that are integrally formed; the central claw rod 12a, the first connecting portion 121 and the second connecting portion 122 are sequentially connected, and the first connecting portion 121 and the second connecting portion 122 both extend along a length direction of the central claw rod 12a. The first connecting portion 121 is provided with a first sliding chute 12c and a first fixing hole 12b, where the first sliding chute 12c is a strip-shaped chute, the first sliding chute 12c extends along a length direction of the first connecting portion 121, one end of the first sliding chute 12c close to the central claw rod 12a has a gap with the central claw rod, and the other end of the first sliding chute 12c away from the central claw rod 12a extends to a connection position of the first connecting portion 121 and the second connecting portion 122. The first fixing hole 12b is located between the central claw rod 12a and the first sliding chute 12c. The second connecting portion 122 is provided with a tail cavity 12d with openings at two ends and a first through hole 12e communicated with the tail cavity 12d, where one port of the tail cavity 12d is communicated with the first siding chute 12c, and the other port of the tail cavity 12d is located at an end surface of the second connecting portion 122 away from the first connecting portion 121. The number of the first through holes 12e is two, and two first through holes 12e are arranged centrosymmetric. Optionally, one end of the second connecting portion 122 away from the first connecting arm is further provided with two locking grooves 12f, and a groove depth of the locking groove 12f extends along a length direction of the second connecting portion 122. Optionally, the two locking grooves 12f are centrosymmetric.

Optionally, two avoidance grooves 123 are arranged symmetrically on a peripheral surface of the central claw rod 12a.

Optionally, the first connecting portion 121 and the central claw rod 12a are both board-shaped structures, and a board surface of the first connecting portion 121 and a board surface of the central claw rod 12a are perpendicular to each other.

Figure 8:
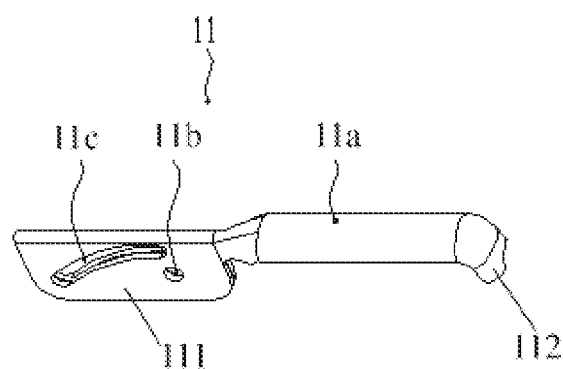
FIG. 8 is a structural schematic diagram of a clamping arm of the present disclosure.

Please refer to FIG. 1 and FIG. 8, optionally, the clamping portion includes a clamping arm 11 and a connecting arm 14, where the connecting arm 14 is movably connected to the clamping arm 11. The clamping arm 11 includes a clamping claw 11 and a third connecting portion 111 which are integrally formed. One end of the clamping claw 11a away from the third connecting portion 111 is bent to form a catching portion 112. The third connecting portion 111 is set to have a board-shaped structure, and the third connecting portion 111 is provided with a second fixing hole 11b and a third sliding chute 11c, and the third sliding chute 11c is an arc-shaped chute. It should be noted that the third sliding chute 11c may be set to have a through-hole structure, and in addition, the third sliding chute 11c may be set as an arc-shaped through-hole structure. Optionally, the connecting arm 14 is provided with a front end connecting hole 14a and a tail end connecting hole 14b, where the front end connecting hole 14a and the tail end connecting hole 14b are spaced along a length direction of the connecting arm 14. The connecting arm 14 is movably fitted with the clamping arm 11 through a first pin shaft 15, optionally, the first pin shaft 15 passes through the front end connecting hole 14a and the third sliding chute 11c at the same time, and a part of the first pin shaft 15 is located inside the first sliding chute 12c, which can reduce an overall volume. During a process of a rotation of the clamping arm 11 relative to the central claw rod 12a, the first pin shaft 15 slides in the third sliding chute 11c so that the clamping arm 11 slides relative to the connecting arm 14, a sliding range of the clamping arm 11 is limited through a cooperation of the first pin shaft 15 and the third sliding chute 11c, thereby limiting a rotating range of the clamping arm 11 relative to the clamping holder 12.

Two clamping arms 11 are respectively located at two sides of the clamping holder 12, and the two clamping arms 11 and the central claw rod 12a of the clamping holder 12 form a dual-clamping structure, where the clamping structure is configured to clamp a human mucosal tissue. Optionally, the two clamping arms 11 are respectively located at two sides of the first connecting portion 121, and the third connecting portion 111 of each clamping arm 11 attaches to the board surface of the first connecting portion 121. After the two clamping arms 11 attach to the clamping holder 12, two second fixing holes 11b on the two third connecting portions 111 are located at two ends of the first fixing hole 12b and are communicated with the first fixing hole 12b at the same time, and a rotatably fit of the clamping arm 11 and the clamping holder 12 is realized by using a fixing pin 13 passing through the first fixing hole 12b and two second fixing holes 11b. When the two clamping arms 11 rotate to a closed position relative to the clamping holder 12, two catching portions 112 on the two clamping arms 11 are respectively caught into the two avoidance grooves 123 on the central claw rod 12a, thus the overall structure is more compact; in a process of clamping a tissue, the tissue forms a bent shape between an end of the catching portion 112 and the avoidance groove 123, thus the clamping is more stable.

Figure 6:
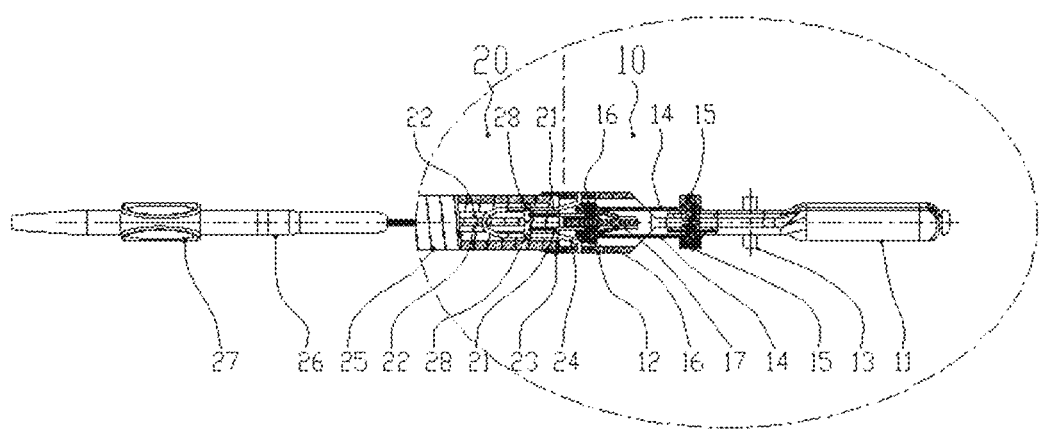
FIG. 6 is a second structural schematic diagram of a closed state of the present disclosure (top view)
Figure 7:
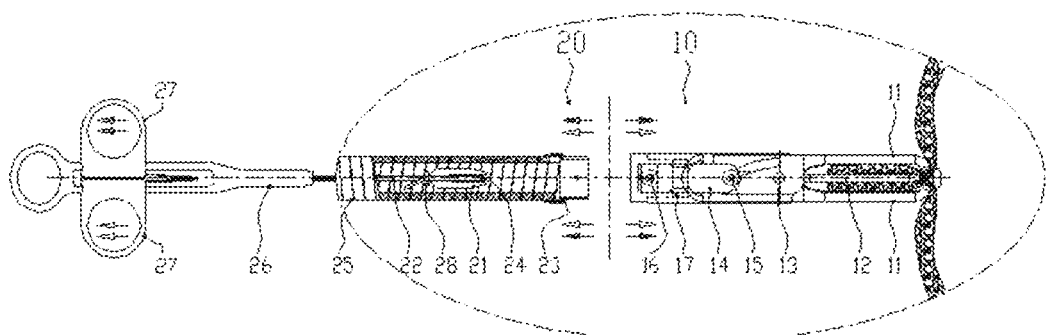
FIG. 7 is a structural schematic diagram of a released state of the present disclosure.

Please refer to FIG. 1 and FIG. 6, in the present disclosure, optionally, the driving assembly 20 includes a driving member 21, where the driving member 21 is movably connected to the connecting arm 14, and the driving member 21 is configured to drive the connecting arm 14 to reciprocate linearly to drive the clamping arm 11 to rotate relative to the clamping holder 12. The driving member 21 is provided with a second sliding chutes 21a, where the second sliding chute 21a is a strip-shaped chute, and when the driving member 21 is connected to the connecting arm 14, the second sliding chute 21a extends along a length direction of the connecting arm 14. In the present disclosure, one end of the connecting arm 14 is movably connected to the clamping arm 11 through the first pin shaft 15 and the other end of the connecting arm 14 is movably connected to the driving member 21 through a second pin shaft 16, that is, the second pin shaft 16 simultaneously passes through the tail end connecting hole 14b of the connecting arm 14 and the second sliding chute 21a so as to connect the connecting arm 14 and the driving member 21. When reciprocating linearly along an extending direction of the second sliding chute 21a, the driving member 21 can drive the connecting arm 14 to reciprocate linearly along the extending direction of the second sliding chute 21a to drive the clamping arm 11 to reciprocate linearly along an extension direction of the third sliding chute 11c, so as to realize opening and closing of the two clamping arms 11. In other words, when the driving member 21 moves close to the connecting arm 14, the driving member 21 can resist against the connecting arm 14 relying on the second pin shaft 16 to drive the connecting arm 14 to move close to the clamping arm 11, and the connecting arm 14 resists against a chute wall of the third sliding chute 11c through the first pin shaft 15 and slides in the third sliding chute 11c. Since the third sliding chute 11c is the arc-shaped chute, when the first pin shaft 15 slides in the third sliding chute 11c, it also drives the clamping arm 11 to rotate around the fixing pin 13 relative to the clamping holder 12, so that the clamping arm 11 is opened. In the same way, when the clamping arm 11 is opened to a maximum angle, the driving member 21 returns back to drive the clamping arm 11 to close through the connecting arm 14.

Optionally, the tail cavity 12d is provided with a locking piece 17, where the locking piece 17 divides the tail cavity 12d to form two sliding channels, the two connecting arms 14 are respectively slidably fitted with the two sliding channels, and the connecting arm 14 and the clamping holder 12 are relatively fixed in a circumferential direction of the tail cavity 12d, that is, the connecting arm 14 only slides back and forth linearly relative to the clamping holder 12, and does not rotate around an axis of the clamping holder 12 relative to the clamping holder 12.

Figure 2:
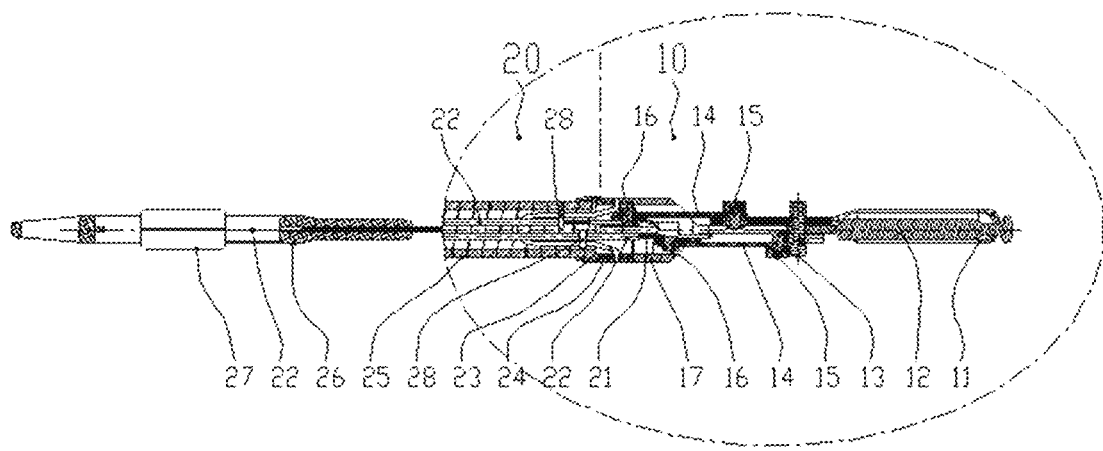
FIG. 2 is a second structural schematic diagram of the present disclosure (top view)
Figure 3:
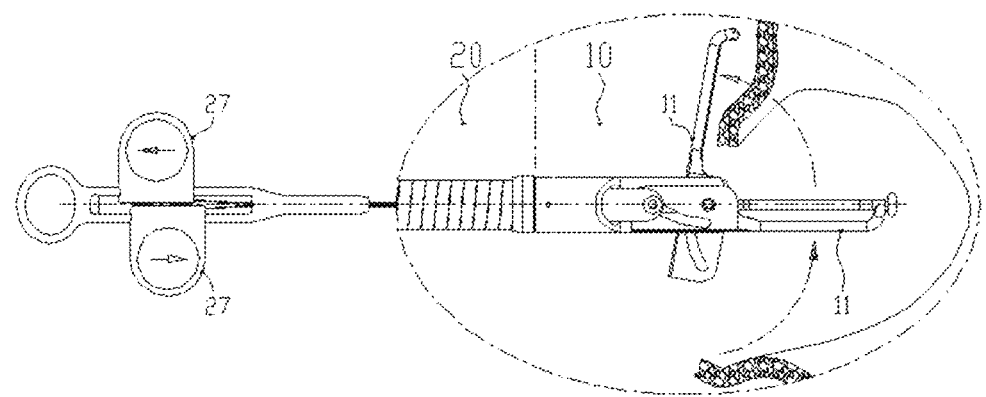
FIG. 3 is a first structural schematic diagram of an open of the present disclosure (one sided clamping)
Figure 4:
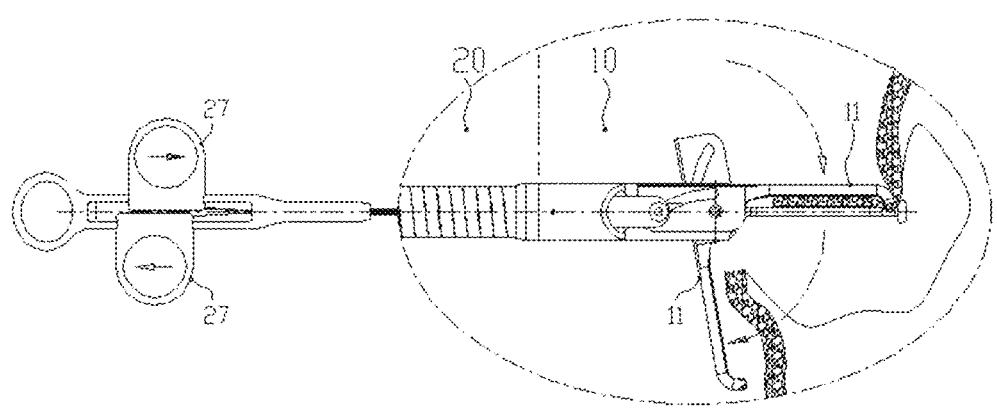
FIG. 4 is a second structural schematic diagram of an open of the present disclosure (dual-sided clamping)
Figure 5:
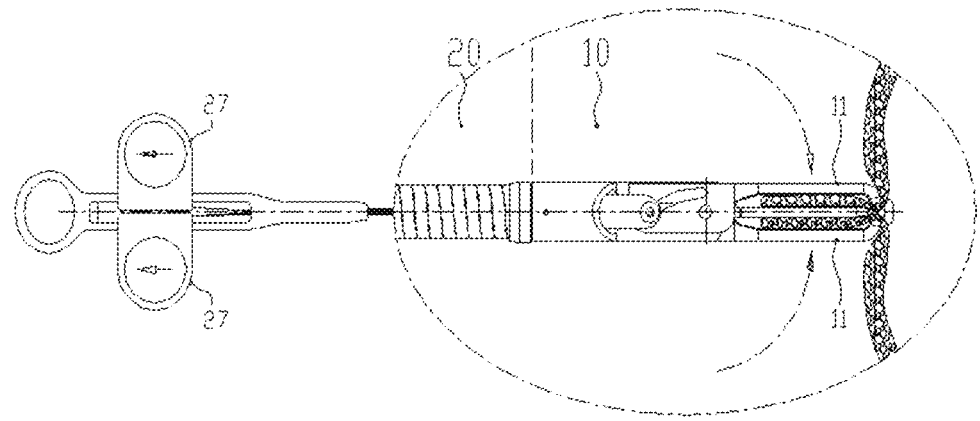
FIG. 5 is a first structural schematic diagram of a closed state of the present disclosure (front view)
Figure 12:
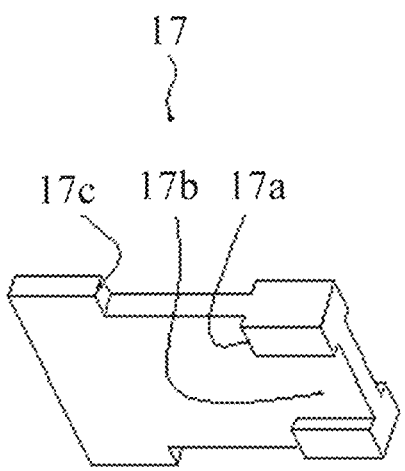
FIG. 12 is a structural schematic diagram of a locking piece of the present disclosure.
Figure 13:
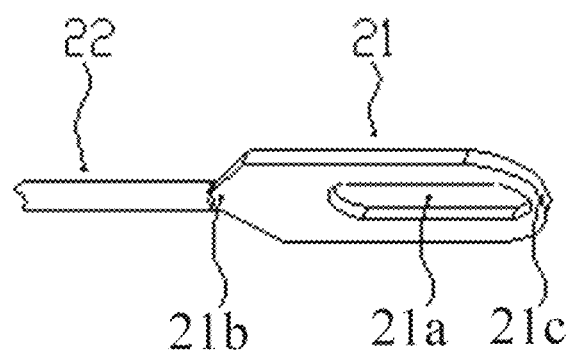
FIG. 13 is a structural schematic diagram of a driving member of the present disclosure.
Figure 14:
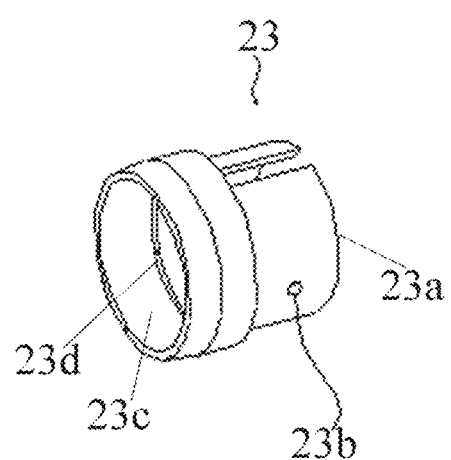
FIG. 14 is a structural schematic diagram of a clamping base of the present disclosure.
Figure 15:
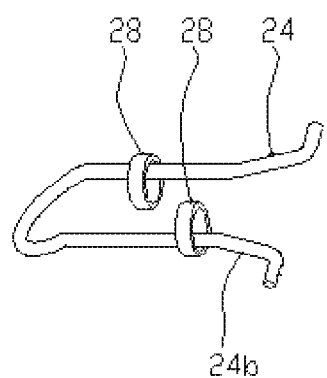
FIG. 15 is a structural schematic diagram of a releasing ring of the present disclosure.

Please refer to FIG. 12, and in conjunction with FIG. 1 and FIG. 2, optionally, the locking piece 17 is board-shaped, and the locking piece 17 may be, but not limited to, a rectangular board. Two board surfaces of the locking piece 17 are respectively provided with a pair of locking platforms 17a, where the pair of locking platform 17a is located on the same board surface are spaced along a width direction of the locking piece 17, and a channel 17b is defined between the pair of locking platforms 17a. Locking blocks 17c are respectively provided on two side surfaces in a width direction of the locking piece 17. The locking piece 17 is inserted into the second connecting portion 122 from a port of the second connecting portion 122 away from the first connecting portion 121, the two locking blocks 17c are respectively snap-fitted with the two locking grooves 12f on the second connecting portion 122, and the two connecting arms 14 are respectively slidably fitted with the two channels 17b, and the two connecting arms 14 cannot rotate relative to the channel 17b.

It should be noted that, when the driving member 21 moves linearly, it can slide into the channel 17b to limit a position of the driving member 21.

In the present disclosure, optionally, the first pin shaft 15 is mainly consist of a first pin body 15a, a first flange 15b and a first pin cap 15c, where the first pin body 15a has a cylindrical structure, and the first pin body 15a and the first flange 15b are integrally formed, and the first flange 15b is located at one end of the first pin body 15a and protrudes outwardly from a peripheral surface of the first pin body 15a along a radial direction of the first pin body 15a. The first pin body 15a simultaneously passes through the front end connecting hole 14a and the third sliding chute 11c, the first pin cap 15c is sleeved outside the first pin body 15a, and works together with the first flange 15b to limit a movement of the clamping arm 11 and the connecting arm 14 in an axial direction of the first pin body 15a, to prevent the clamping arm 11 and the connecting arm 14 from falling off from an end of the first pin body 15a. The first pin cap 15c and the first pin body 15a are configured to be detachably connected to facilitate installation and replacement. When the connecting arm 14 moves linearly, the first pin body 15a is driven to slide in the third sliding chute 11c, so that the first pin body 15a drives the clamping arm 11 to rotate relative to the clamping holder 12, thus the clamping arm 11 is opened or closed.

In the present disclosure, optionally, the second pin shaft 16 is mainly consist of a second pin body 16a, a second flange 16b, and a second pin cap 16c, where the second pin body 16a has a cylindrical structure, and the second pin body 16a and the second flange 16b are integrally formed, and the second flange 16b is located at one end of the second pin body 16a and protrudes outwardly from a peripheral surface of the second pin body 16a along a radial direction of the second pin body 16a. The second pin body 16a simultaneously passes through the tail end connecting hole 14b and the second sliding chute 21a, the second pin cap 16c is sleeved outside the second pin body 16a, and works together with the second flange 16b to limit a movement of the clamping arm 11 and the connecting arm 14 in an axial direction of the second pin body 16a, to prevent the clamping arm 11 and the connecting arm 14 from falling off from an end of the second pin body 16a. The second pin cap 16c and the second pin body 16a are configured to be detachably connected to facilitate installation and replacement. When the driving member 21 moves linearly, the second pin body 16a slides in the second sliding chute 21a, and the second pin body 16a can resist against a chute wall of the second sliding chute 21a to drive the connecting arm 14 to move linearly through the second pin body 16a, and the linear movement of the connecting arm 14 drives the clamping arm to rotate relative to the clamping holder 12, so that the clamping arm 11 is opened or closed.

Optionally, the fixing pin 13 includes a third pin body 13a, a third flange 13b, and a third pin cap 13c, where the third pin body 13a has a cylindrical structure, and the third pin body 13a and the third flange 13b are integrally formed, and the third flange 13b is located at one end of the third pin body 13a, and protrudes outwardly from a peripheral surface of the third pin body 13a along a radial direction of the third pin body 13a. The third pin body 13a simultaneously passes through the first fixing hole 12b and the second fixing hole 11b, and the third pin cap 13c is sleeved outside the third pin body 13a, and works together with the third flange 13b to limit a movement of the clamping arm 11 and the center claw rod 11a in an axial direction of the third pin body 13a, to prevent the clamping arm 11 and the center claw rod 11a from falling off from an end of the third pin body 13a. The third pin cap 13c and the third pin body 13a are configured to be detachably connected to facilitate installation and replacement. When the connecting arm 14 moves linearly, the clamping arm 11 is driven to rotate around an axis of the third pin body 13a, so that the clamping arm 11 is opened or closed.

Figure 11:
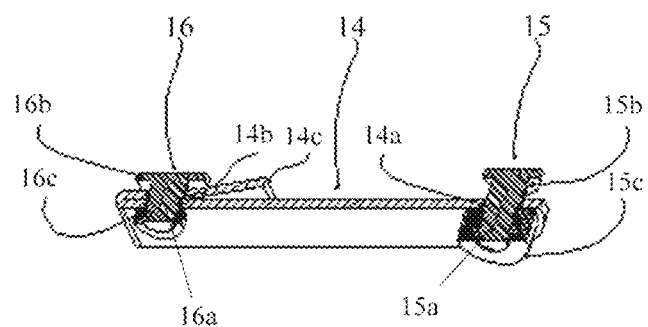
FIG. 11 is a structural schematic diagram of a connecting arm of the present disclosure.

Referring to FIG. 11 and in conjunction with FIG. 2, in the present disclosure, optionally, a tail end of the connecting arm 14 is provided with an elastic piece 14c having elastic, and the locking platform 17a of the locking piece 17 and the elastic piece 14c of the connecting arm 14 constitute a pawl structure. In other words, the locking platform 17a and the elastic piece 14c constitute an anti-return structure that restricts the connecting arm 14 from driving the clamping arm 11 to rotate from a closed state to an open state: when the clamping arm 11 is at a closed position, the elastic piece 14c on the connecting arm 14 is located between the connecting arm 14 and the locking piece 17, and one side of the elastic piece 14c away from the connecting arm 14 is bent toward the locking piece 17, so that an orthographic projection of the elastic piece 14c in an axial direction of the tail cavity 12d at least partially overlaps with the locking platform 17a, and the elastic piece 14c is at least partially located at a sliding path of the driving member 21. When the connecting arm 14 has a tendency of moving forward, an end of the elastic piece 14c resists against the locking platform 17a to prevent the connecting arm 14 from moving forward and further locks the clamping arm 11 connected with the connecting arm 14 to keep the clamping arm 11 closed; when the driving member 21 moves forward, since the second sliding chute 21a is provided on the driving member 21, the second sliding chute 21a is set to have a first chute wall close to the connecting arm 14 and a second chute wall away from the connecting arm 14 in a length direction thereof, the second pin shaft 16 has a gap with the second chute wall of the second sliding chute 21a, and the second pin shaft 16 can slide close to the second chute wall in the second sliding chute 21a without an external force acting on the connecting arm 14, that is, the connecting arm 14 will not interfere with the movement of the driving member 21, the driving member 21 can move close to the connecting arm 14 and squeeze the elastic piece 14c, so that the elastic piece 14c is deformed under an action of the driving member 21 and moves close to the connecting arm 14, so that the orthographic projection of the elastic piece 14c in the axial direction of the tail cavity 12d does not overlap with the locking platform 17a, thus a locking between the elastic piece 14c and the locking platform 17a is dismantled. When the driving member 21 continues to move forward, the second chute wall of the second sliding chute 21a moves and resists against the second pin shaft 16, and the driving member 21 can transmit an external force to the second pin shaft 16 through the second chute wall by continuing to move forward, thereby pushing the connecting arm 14 to move forward by using the second pin shaft 16, and the first pin shaft 15 connected with the connecting arm 14 slides in the third sliding chute 11c under a push of the connecting arm 14 and drives the clamping arm 11 to rotate around the fixing pin 13 to open the connecting arm 14

When the clamping arm 11 is opened and needs to be closed, the driving member 21 returns back, the driving member 21 cancels a resisting force on the elastic piece 14c, and the elastic piece 14c returns to a inclined state toward the locking platform 17a, to realize a locking of the connecting arm 14, and prevent the connecting arm 14 from opening automatically after being closed.

In the present disclosure, optionally, a detachable connection between the driving assembly and the clamping assembly is achieved through a hook 24.

Optionally, the conjoined dual-clamp further includes a clamping base 23, where the clamping base 23 is configured to be detachably connected with the second connecting portion 122, and the clamping base 23 is configured to be detachably connected with a spring hose 25. Optionally, the clamping base 23 has a hollow structure, and the clamping base 23 includes a hollow insertion portion 23a and a hollow sleeved portion 23c, where the insertion portion 23a is communicated with the sleeved portion 23c, an outer diameter of the insertion portion 23a is smaller than an outer diameter of the sleeved portion 23c, and an inner diameter of the insertion portion 23a is smaller than an inner diameter of the sleeved portion 23c, and a stepped structure 23d is formed between an inner peripheral wall of the insertion portion 23a and an inner peripheral wall of the sleeved portion 23c. When assembling, the insertion portion 23a is inserted into the second connecting portion 122, the spring hose 25 is inserted into the sleeved portion 23c. The insertion portion 23a is provided with a second through hole 23b.

Optionally, the driving assembly 20 further includes two flexible shafts 22, two hook arms 24b of the hook 24 are respectively provided with a releasing ring 28, and the two flexible shafts are fitted with two releasing rings 28 one by one, and a front end of each flexible shaft respectively passes through corresponding releasing ring 28 and is connected to the driving member 21. A front end of the driving member is provided with a fracture region 21c, a rear end of the flexible shaft 22 is respectively connected to a slip ring 27, and the slip ring 27 is sleeved on the handle 26, a rear end of the clamping base 23 is connected to the spring hose 25, and the two flexible shafts 22 are provided in the spring hose 25. The slip ring 27 is pulled to fracture the driving member 21 under a predetermined pull, the tail end 21b of the driving member 21 that continues to move backward sequentially drives the releasing ring 28 and the hook 24 to move backward, and the hook 24 is sequentially separated from the first through hole 12e of the clamping holder 12 and the second through hole 23b of the clamping base, and a connection between the clamping holder 12 and the clamping base 23 is dismantled and the clamping holder 12 and the clamping base 23 are separated.

Optionally, an operation method of the hemostasis and suturing conjoined dual-clamp capable of passing through the channel of the digestive endoscope includes an opening method, a closing method, a locking method and a disassembling method of the dual-clamp;

optionally, the opening method of the conjoined dual-clamp is: the driving member 21 is pushed to move forward, and the driving member 21 moves forward to drive the connecting arm 14 to move forward, so that the clamping arm 11 rotates and opens to facilitate subsequent clamping of a human mucosal tissue;

optionally, the closing method of the conjoined dual-clamp is: when the clamping arm 11 is opened and needs to be closed, the driving member 21 is pulled backward to make the driving member 21 to move backward to drive the connecting arm 14 to move backward, thereby driving the clamping arm 11 to rotate in a reverse direction, and the clamping arm 11 is closed and clamps the human mucosal tissue;

optionally, the locking method of the conjoined dual-clamp is: after the closing step is completed, the driving member 21 is continuously pulled backward, and the driving member 21 cancels a force acting on the elastic piece 14c of the connecting arm 14, and the elastic piece 14c rebounds and is locked on the locking platform 17a of the locking piece 17 after losing a pressure of the driving member 21, and the driving member 21 and the clamping arm 14 are kept in a relative position and locked; and optionally, the disassembling method of the conjoined dual-clamp is: after the locking step is completed, the driving member 21 is continuously pulled backward with a greater pulling force to fracture the driving member 21, and a connection between the driving assembly 20 and the clamping assembly 10 is dismantled and the driving assembly 20 and the clamping assembly 10 are separated.

Optionally, the opening method of the conjoined dual-clamp is: the slip ring 27 is pushed forward, to sequentially push the flexible shaft 22 and the driving member 21 to move forward, the driving member 21 moves forward to pass through a channel 17b of the locking piece 17, and the driving member 21 moves forward relative to the connecting arm 14. In this process, the driving member 21 will not drive the connecting arm 14 to move forward, and the driving member 21 can press down the elastic piece 14c on the connecting arm 14 so that the elastic piece 14c moves close to the connecting arm 14, the locking between the elastic piece 14c of the connecting arm 14 and the locking platform 17a of the locking piece 17 is dismantled. And then the driving member 21 is continued to be pushed, the driving member 21 can drive the connecting arm 14 to move forward and push the first pin shaft 15 to slide in the third sliding chute 11c of the clamping arm 11, to drive the clamping arm 11 to rotate and open, and an opening formed by the clamping claw 11a of the clamping arm 11 and the central claw rod 12a of the clamping holder 12 is opened to facilitate subsequent clamping of the human mucosal tissue.

In the present disclosure, when the conjoined dual-clamp is opened, the connecting arm 14 is located on an outer side of the tail cavity 12d of the clamping holder 12.

Optionally, the closing method of the conjoined dual-clamp is: when the clamping arm 11 is opened and needs to be closed, the slip ring 27 is pulled backward, to sequentially pull the flexible shaft 22, the driving member 21 and the connecting arm 14, and the first pin shaft 15 of the connecting arm 14 moves backward in the third sliding chute 11c of the clamping arm 11, to drive the clamping arm 11 to rotate and close, and the opening formed by the clamping claw 11a of the clamping arm 11 and the central claw rod 12a of the clamping holder 12 is closed and the human mucosal tissue can be clamped;

in the present disclosure, when the conjoined dual-clamp is closed, one end of the connecting arm 14 is located on the outer side of the tail cavity 12d of the clamping holder 12, and the other end is located inside the tail cavity 12d.

Optionally, the locking method of the conjoined dual-clamp is: after the closing step is completed, the driving member 21 is continuously pulled backward, the driving member 21 moves backward relative to the connecting arm 14, and the driving member 21 cancels the force acting on the elastic piece 14c, the elastic piece 14c rebounds after losing the pressure of the driving member 21, the elastic piece 14c of the connecting arm 14 is locked on the locking platform 17a of the locking piece 17, and the connecting arm 14, the first pin shaft 15 and the clamping arm 11 are kept in a relative position and locked.

Optionally, the disassembling method of the conjoined dual-clamp is: after the locking step is completed, the driving member 21 is continuously pulled backward with a greater pulling force, the narrow fracture region 21c of a front portion of the driving member 21 is fractured, and tail end 21b of the driving member 21 that continues to move backward sequentially drives the releasing ring 28 and the hook 24 to move backward, the hook 24 is sequentially separated from the first through hole 12e on the clamping holder 12 and the second through hole 23b on the clamping base 23, and a connection between the clamping holder 12 and the clamping base 23 is dismantled and the clamping holder 12 and the clamping base 23 are separated.

Obviously, the foregoing embodiments are merely examples for clearly describing, and are not intended to limit the implementations. For those skilled in the art, other changes or variations in different forms can be made on the basis of the above description. No need to be exhaustive here. Obvious changes or variations derived from herein are still within the scope of protection of the present disclosure.

INDUSTRIAL APPLICABILITY

In summary, the present disclosure provides a hemostasis and suturing conjoined dual-clamp capable of passing through a channel of a digestive endoscope and an operation method, which are convenient and reliable to operate.

What is claimed is:

1. A hemostasis and suturing conjoined dual-clamp capable of passing through a channel of a digestive endoscope, comprising: a handle, a clamping assembly and a driving assembly, wherein the clamping assembly is provided at a front end of the handle, the clamping assembly comprises a clamping holder and two clamping portions, the two clamping portions are provided around two sides of the clamping holder and are rotatably connected to the clamping holder, the driving assembly is configured to drive the two clamping portions to open and close relative to the clamping holder, respectively; the driving assembly is detachably connected to the clamping assembly; and wherein the clamping holder comprises a central claw rod, a first connecting portion and a second connecting portion that are sequentially connected, the second connecting portion is provided with a tail cavity with openings at two ends; and the two clamping portions both pass through the tail cavity and are located at two sides of the first connecting portion, and the two clamping portions are rotatably fitted with the first connecting portion.

2. The hemostasis and suturing conjoined dual-clamp capable of passing through the channel of the digestive endoscope according to claim 1, wherein the clamping holder is provided with a first fixing hole, and each of the two clamping portions is provided with a second fixing hole; the clamping holder further comprises a fixing pin, wherein the fixing pin simultaneously passes through the first fixing hole and the second fixing holes of the two clamping portions to connect with the central claw rod and the two clamping portions.

3. The hemostasis and suturing conjoined dual-clamp capable of passing through the channel of the digestive endoscope according to claim 1, wherein a peripheral surface of the central claw rod is provided with two avoidance grooves, and the two clamping portions are each protrudingly provided with a catching portion, and when the two clamping portions are closed, the catching portions on the two clamping portions are respectively caught into the two avoidance grooves.

4. The hemostasis and suturing conjoined dual-clamp capable of passing through the channel of the digestive endoscope according to claim 1, wherein each of the two clamping portions comprises a clamping arm and a connecting arm, wherein each connecting arm is movably connected to the respective clamping arm, the driving assembly is connected to each connecting arm, and the driving assembly is configured to drive each connecting arm to move so as to drive the clamping arms to rotate relative to the clamping holder.

5. The hemostasis and suturing conjoined dual-clamp capable of passing through the channel of the digestive endoscope according to claim 4, wherein the driving assembly is configured to drive each connecting arm to reciprocate linearly, so that the connecting arms drive the clamping arms to rotate relative to the clamping holder.

6. The hemostasis and suturing conjoined dual-clamp capable of passing through the channel of the digestive endoscope according to claim 5, wherein each clamping arm comprises a clamping claw and a third connecting portion which are connected, wherein each third connecting portion is provided with a third sliding chute, an extending direction of each third sliding chute has an angle with a sliding direction of the respective connecting arm, and the connecting arms are slidably fitted with the third sliding chutes, and when the driving assembly drives the connecting arms to move linearly, the connecting arms slide in the respective third sliding chute and meanwhile drive the clamping arms to rotate.

7. The hemostasis and suturing conjoined dual-clamp capable of passing through the channel of the digestive endoscope according to claim 6, wherein each connecting arm is provided with a front end connecting hole, and the clamping assembly further comprises a first pin shaft, wherein the first pin shaft simultaneously passes through the respective front end connecting hole and the respective third sliding chute, to connect with the respective third connecting portion and the respective connecting arm.

8. The hemostasis and suturing conjoined dual-clamp capable of passing through the channel of the digestive endoscope according to claim 4, wherein the clamping assembly further comprises a locking piece, wherein the locking piece is connected to the clamping holder and forms two independent sliding channels together with the clamping holder, the connecting arms respectively pass through the two independent sliding channels, and the connecting arms and the clamping holder are relatively fixed on a circumferential direction of the clamping holder.

9. The hemostasis and suturing conjoined dual-clamp capable of passing through the channel of the digestive endoscope according to claim 8, wherein the locking piece is snap-fitted with the clamping holder.

10. The hemostasis and suturing conjoined dual-clamp capable of passing through the channel of the digestive endoscope according to claim 8, wherein the clamping assembly further comprises an anti-return structure, wherein the anti-return structure is provided between the connecting arms and the locking piece and is configured to restrict the connecting arms from driving the clamping arms to rotate from a closed state to an open state.

11. The hemostasis and suturing conjoined dual-clamp capable of passing through the channel of the digestive endoscope according to claim 10, wherein the anti-return structure comprises an elastic piece and a locking platform, wherein the locking piece has two opposite board surfaces, and each of the board surfaces is provided with the locking platform; each connecting arm is connected to one side of the elastic piece, and when the clamping arms are closed, the other side of the elastic piece is located between the locking platform and the driving assembly, and the other side of the elastic piece is inclined in a direction away from the connecting arms, so that an orthographic projection of the elastic piece in a sliding direction of the connecting arms at least partially overlaps with the locking platform, to restrict the connecting arms from passing over the elastic piece in a direction close to the elastic piece.

12. The hemostasis and suturing conjoined dual-clamp capable of passing through the channel of the digestive endoscope according to claim 11, wherein the driving assembly comprises two driving members, the two driving members are fitted with the two connecting arms one by one, and each driving member is provided with a sliding chute, the clamping assembly further comprises a second pin shaft, the driving assembly and the connecting arms are both connected to the second pin shaft, and the second pin shaft passes through the sliding chutes and is slidably fitted with the respective sliding chute; and the driving assembly is configured to press the elastic piece to unlock the elastic piece from the locking platform when sliding relative to the connecting arms, and drive the connecting arms to move linearly through the second pin shaft after unlocking the elastic piece from the locking platform, to enable the clamping arms to rotate.

13. The hemostasis and suturing conjoined dual-clamp capable of passing through the channel of the digestive endoscope according to claim 11, wherein the elastic piece and at least one of the connecting arms are integrally formed.

14. The hemostasis and suturing conjoined dual-clamp capable of passing through the channel of the digestive endoscope according to claim 12, wherein each driving member is provided with a fracture region, and each fracture region is located at one side of the respective sliding chute close to the respective connecting arm.

15. The hemostasis and suturing conjoined dual-clamp capable of passing through the channel of the digestive endoscope according to claim 1, further comprising a clamping base, the clamping base is detachably connected to the clamping holder.

16. The hemostasis and suturing conjoined dual-clamp capable of passing through the channel of the digestive endoscope according to claim 1, further comprising a hook, and the driving assembly is detachably connected to the clamping assembly through the hook.

17. The hemostasis and suturing conjoined dual-clamp capable of passing through the channel of the digestive endoscope according to claim 16, wherein the driving assembly further comprises two flexible shafts, two hook arms of the hook are respectively provided with a releasing ring, one end of the two flexible shafts respectively pass through corresponding releasing rings, and the other end of the two flexible shafts are respectively connected to the two clamping portions.

18. An operation method of the hemostasis and suturing conjoined dual-clamp capable of passing through the channel of the digestive endoscope according to claim 1, wherein the operation method comprises an opening method, a closing method, a locking method, and a disassembling method of the dual-clamp; the opening method is: pushing a driving member of the driving assembly to move forward, and driving a connecting arm of the clamping assembly to move forward by movement forward of the driving member, so that the connecting arm rotates and opens to facilitate subsequent clamping of a human mucosal tissue; the closing method is: pulling the driving member to move backward to drive the connecting arm to move backward, so that the connecting arm rotates and is closed, and a clamping arm of the clamping assembly is closed and clamps the human mucosal tissue; the locking method is: after the closing step is completed, continuing to pull the driving member backward, so that an elastic piece of the connecting arm rebounds and is locked on a locking platform of a locking piece after losing a pressure of the driving member, and the driving member and the clamping arm are kept in a relative position and locked; and the disassembling method is: after the locking step, continuing to pull the driving member to move backward with a greater pulling force to make the driving member fractured, to dismantle a connection between the driving assembly and the clamping assembly and to separate the driving assembly and the clamping assembly.

19. The operation method of the hemostasis and suturing conjoined dual-clamp capable of passing through the channel of the digestive endoscope according to claim 18, wherein the opening method further comprises pushing a slip ring forward, to sequentially push two flexible shafts of the driving assembly and the driving member to move forward, wherein the driving member moves forward to pass through a channel of the locking piece, and presses down the elastic piece on the connecting arm to release the lock of the locking platform of the locking piece, the connecting arm moves forward to push the clamping arm to rotate so as to open an opening formed with the central claw rod of the clamping holder, to facilitate the subsequent clamping of the human mucosal tissue; the closing method further comprises pulling a slip ring backward to sequentially pull the two flexible shafts, the driving member and the connecting arm to move backward, so as to drive the clamping arm to rotate to close the opening formed with the central claw rod of the clamping holder, to clamp the human mucosal tissue by closing; the locking method further comprises, after the closing step is completed, continuing to pull the driving member backward, so that the driving member moves backward relative to the connecting arm, the elastic piece of the connecting arm rebounds and is locked on the locking platform of the locking piece after losing the pressure of the driving member, and the connecting arm and the clamping arm are kept in a relative position and locked; and the disassembling method is: further comprises after the locking step is completed, continuing to pull the driving member backward in a direction of closing the clamping arm to make a fracture region of the driving member fractured, wherein a tail end of the driving member drives two releasing rings and a hook to move backward after the fracture region is fractured, until the hook is separated from a through hole of the clamping holder and a clamping base, and thus dismantle a connection between the clamping holder and the clamping base and separate the clamping holder and the clamping base.

\* \* \* \* \*